(12) United States Patent
Itagaki

(10) Patent No.: US 7,252,635 B2
(45) Date of Patent: Aug. 7, 2007

(54) BIOLOGICAL DATA ACQUIRING APPARATUS

(75) Inventor: Shuji Itagaki, Asaka (JP)

(73) Assignee: Tanita Corporation, Tokyo (JP)

( * ) Notice: Subject to any disclaimer, the term of this patent is extended or adjusted under 35 U.S.C. 154(b) by 163 days.

(21) Appl. No.: 10/863,230

(22) Filed: Jun. 9, 2004

(65) Prior Publication Data

US 2004/0254496 A1    Dec. 16, 2004

(30) Foreign Application Priority Data

Jun. 16, 2003    (JP)    ............... 2003-170171

(51) Int. Cl.
*A61B 5/00*    (2006.01)

(52) U.S. Cl. .................... 600/300; 600/301

(58) Field of Classification Search ........ 600/300–301, 600/546; 128/920
See application file for complete search history.

(56) References Cited

U.S. PATENT DOCUMENTS

| 6,539,310 B2 | 3/2003 | Shimomura |
| 2001/0053883 A1 | 12/2001 | Yoshimura et al. |

FOREIGN PATENT DOCUMENTS

| EP | 1 201 187 A1 | 5/2002 |
| JP | 10-192258 | 7/1998 |
| JP | P2000-14828 | 1/2000 |
| JP | P2001-224569 | 8/2001 |
| JP | P2002-125947 | 5/2002 |

OTHER PUBLICATIONS

Antonio Piccoli et al., "Impedance Vector Distribution by Sex, Race, Body Mass Index, and Age in the United States: Standard Reference Intervals as Bivariate Z Scores", Nutrition, vol. 18, No. 2, Feb. 2, 2002, pp. 153-167 (XP-002298438).

J.C.K. Wells et al., "The Contribution of Fat and Fat-Free Tissue to Body Mass Index in Contemporary Children and the Reference Child", International Journal of Obesity and Related Metabolic Disorders: Journal of the International Association for the Study of Obesity, vol. 26, No. 10, Oct. 2002, pp. 1323-1328, (XP-002298437).

*Primary Examiner*—Max F. Hindenburg
*Assistant Examiner*—Michael C. Astorino
(74) *Attorney, Agent, or Firm*—McDermott Will & Emery LLP

(57) ABSTRACT

A biological data acquiring apparatus comprises: age data acquiring means, biological data acquiring means, biological data displaying means, and reference data storing means, wherein the age data acquiring means acquires age data of a user, the biological data acquiring means acquires at least two kinds of biological data other than the age data from the user, the biological data displaying means displays the acquired biological data of the user in a graph region whose axes represent these two kinds of biological data, the reference data storing means stores reference data related to at least either of these two kinds of biological data in relation to age, and the biological data displaying means displays the reference data corresponding to the age data of the user in the graph region.

4 Claims, 5 Drawing Sheets

FIG.6A

☐ YOUR TOTAL MUSCLE MASS WITH RESPECT TO FAT PERCENTAGE IS COMPARABLE TO THOSE OF YOUNGSTERS.

☐ AS WE GROW OLDER, FATS ARE APT TO ACCUMULATE IN OUR BODIES AND OUR MUSCLES ARE APT TO DWINDLE.

☐ GIVE FIRST PRIORITY TO KEEP CURRENT MUSCLES.

FIG.6B

☐ YOUR TOTAL MUSCLE MASS WITH RESPECT TO FAT PERCENTAGE IS GETTING CLOSER TO THOSE OF MIDDLE AGE.

☐ IN THE CURRENT SITUATION, YOUR BODY LACKS A MUSCLE MASS TO FULLY CONSUME ENERGY TAKEN INTO YOUR BODY, SO THAT MORE FATS WILL BE ACCUMULATED IN YOUR BODY AND THE RISK OF DEVELOPING LIFESTYLE-RELATED DISEASES WILL BE INCREASED.

☐ TRY TO LOSE FATS IN YOUR BODY.

BIOLOGICAL DATA ACQUIRING APPARATUS

BACKGROUND OF THE INVENTION (i) Field of the Invention

The present invention relates to an apparatus which acquires and displays the biological data of a user. More specifically, it relates to an apparatus which acquires two kinds of biological data of a user and displays the data graphically.

(ii) Description of the Related Art

Apparatuses are proposed to acquire two kinds of biological data of a user and display them in a graph region whose vertical and horizontal axes represent these two kinds of biological data (refer to Patent Publications 1 to 4, for example).

An apparatus disclosed in Patent Publication 1 acquires the body mass index and body fat percentage of a user as the two kinds of biological data and displays the data in a graph region whose horizontal axis represents a body mass index and vertical axis represents a body fat percentage. To display the data, the vertical and horizontal axes are sectioned by given evaluation reference values so as to form a plurality of intersecting sections, and an intersecting section corresponding to the acquired body mass index and body fat percentage of the user is lit. Further, an apparatus disclosed in Patent Publication 2 or 3 acquires the body fat percentage and body weight of a user and displays the acquired data in a graph region whose axes represent the data. Further, an apparatus disclosed in Patent Publication 4 acquires the body mass index of a user and an index related to the fat mass or fat free mass of the user and displays the data in a graph region whose axes represent the data. In addition, in the apparatus of Patent Publication 4, comments corresponding to the acquired biological data of the user are displayed. These conventional apparatuses display two kinds of biological data of a user as an intersection point or an intersecting section in a graph region whose vertical and horizontal axes represent these two kinds of biological data so as to present a comprehensive guideline for health care to the user based on the two kinds of biological data.

Patent Publication 1
  JP-A 10-192258 (the term "JP-A" as used herein means an "unexamined published Japanese patent application")
Patent Publication 2
  JP-A 2000-14828
Patent Publication 3
  JP-A 2001-224569
Patent Publication 4
  JP-A 2002-125947

In view of health care, a number of biological data have different meanings according to age. For example, a high body fat percentage at young age substantially warns a user of a possibility of developing lifestyle-related diseases, while a low body fat percentage at old age substantially warns a user of a possibility of becoming skinny due to aging. Further, in view of health care, understanding one's own biological data by comparing the biological data with those of others at the same age or in the same generation encourages gives the user encouragement and motivation to maintain or improve his health condition.

However, in the conventional apparatuses disclosed in Patent Publications 1 to 4, evaluation reference values which divide the graph regions and comments corresponding to the divided sections are constant regardless of the age of a user. Further, these apparatuses do not display information of how different the biological data of a user which are displayed in the graph regions are from those of others at the same age or in the same generation as that of the user. Thus, these apparatuses do not give sufficient consideration to the age of a user, and it can be therefore hardly said that these apparatuses are capable of presenting health care guidelines suited for users.

Therefore, an object of the present invention is to provide a biological data acquiring apparatus which acquires two kinds of biological data of a user and can display the acquired data in a graph region whose vertical and horizontal axes represent these two kinds of biological data in a manner taking the age of the user into consideration so as to present the user with a health care guideline which is more suited for the user.

SUMMARY OF THE INVENTION

According to one aspect of the present invention, a biological data acquiring apparatus of the present invention comprises:

age data acquiring means,
biological data acquiring means,
biological data displaying means, and
reference data storing means, wherein the age data acquiring means acquires age data of a user, the biological data acquiring means acquires at least two kinds of biological data other than the age data from the user, the biological data displaying means displays the acquired biological data of the user in a graph region whose axes represent these two kinds of biological data, the reference data storing means stores reference data related to at least either of these two kinds of biological data in relation to age, and the biological data displaying means displays the reference data corresponding to the age data of the user in the graph region.

Further, in the biological data acquiring apparatus of the present invention, the reference data are thresholds predetermined for at least either of the two kinds of biological data.

Further, in the biological data acquiring apparatus of the present invention, the reference data are averages for each age or each age range which have been acquired from a number of subjects for at least either of the two kinds of biological data.

Further, in the biological data acquiring apparatus of the present invention, the reference data are referential lines acquired by using smoothing methods, the referential lines being obtained by plotting the two kinds of biological data acquired from a number of subjects in advance in the graph region for each age or each age range and then smoothing the plotted data.

Alternatively, according to another aspect of the present invention, a biological data acquiring apparatus of the present invention comprises:

age data acquiring means,
biological data acquiring means,
biological data displaying means, and
comment data storing means, wherein the age data acquiring means acquires age data of a user, the biological data acquiring means acquires at least two kinds of biological data other than the age data from the user, the biological data displaying means displays the acquired biological data of the user in a graph region whose axes represent these two kinds of biological data, the comment data storing means stores comment data related to at least either of these two kinds of biological data in relation to age, and the biological data displaying means displays the comment data corresponding to the age data of the user.

Further, in the biological data acquiring apparatus of the present invention, each of the two kinds of biological data is any of a body weight, a body mass index, a body fat mass, a body fat percentage, a total body water, a body water percentage, a muscle mass, a muscle percentage, a bone mass, a bone density, a basal metabolic rate and BCM (Body Cell Mass).

BRIEF DESCRIPTION OF THE DRAWINGS

FIGS. 6A and 6B are diagrams showing still other examples of screen displays in the biological data acquiring apparatus of FIG. 1.

DETAILED DESCRIPTION OF THE PREFERRED EMBODIMENTS

Figure 1:
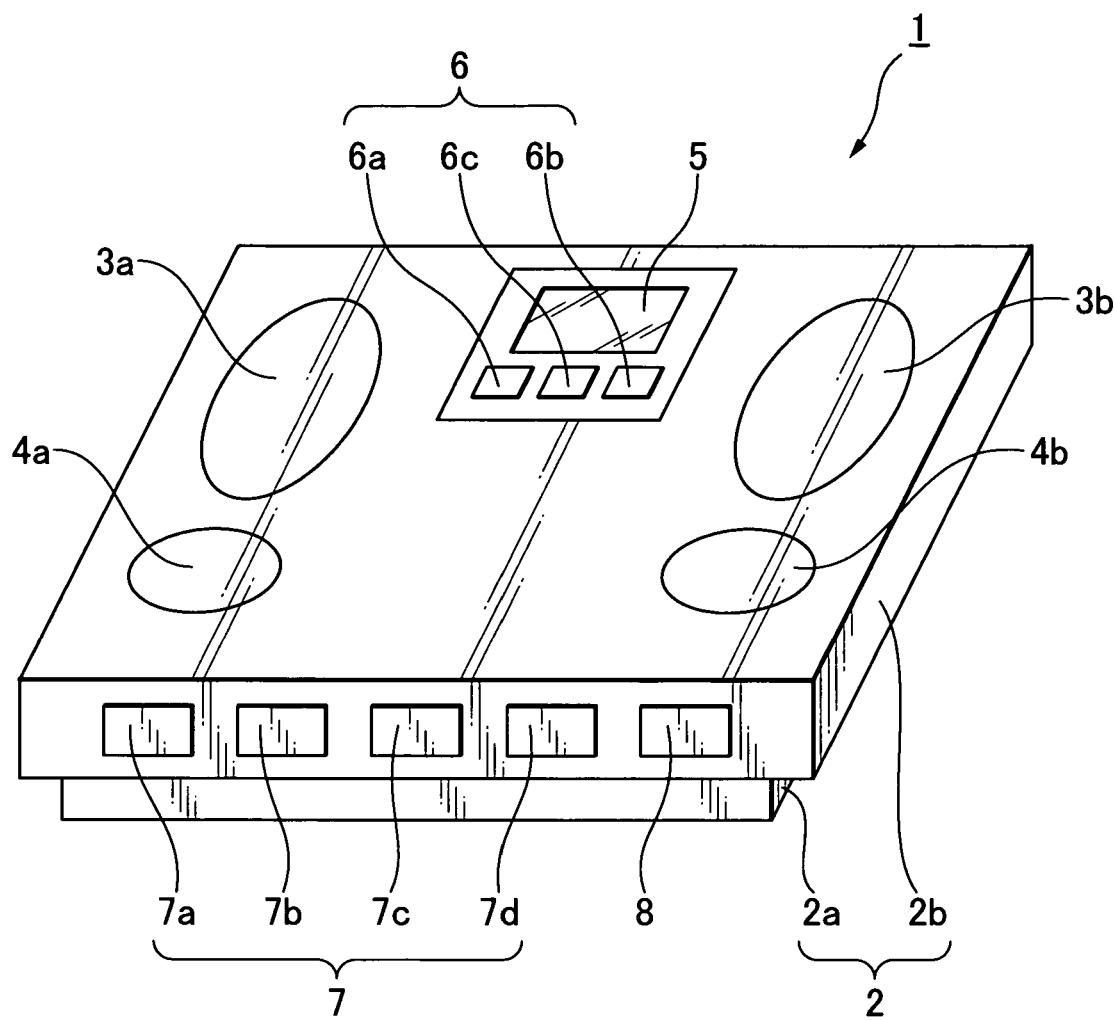
FIG. 1 is an external perspective view of a biological data acquiring apparatus as one embodiment of the present invention.

A biological data acquiring apparatus according to one aspect of the present invention comprises:
age data acquiring means,
biological data acquiring means,
biological data displaying means, and
reference data storing means, wherein
the age data acquiring means acquires age data of a user,
the biological data acquiring means acquires at least two kinds of biological data other than the age data from the user, the biological data displaying means displays the acquired biological data of the user in a graph region whose axes represent these two kinds of biological data, the reference data storing means stores reference data related to at least either of these two kinds of biological data in relation to age, and the biological data displaying means displays the reference data corresponding to the age data of the user in the graph region. Thus, since the biological data of the user are displayed, together with the reference data corresponding to the age data of the user, in the graph region whose axes represent the two kinds of biological data, an appropriate guideline for health care based on the age of the user can be presented to the user.

The reference data are preferably thresholds predetermined for at least either of the two kinds of biological data, averages for each age or each age range which have been acquired from a number of subjects for at least either of the two kinds of biological data, or referential lines which are obtained by plotting the two kinds of biological data acquired from a number of subjects in advance in the graph region for each age or each age range and then smoothing the plotted data. In these cases, since the biological data of the user are displayed in the graph region together with the thresholds, averages or referential lines corresponding to the age data of the user, an appropriate guideline for health care based on the age of the user can be presented to the user.

Alternatively, a biological data acquiring apparatus according to another aspect of the present invention comprises:
age data acquiring means,
biological data acquiring means,
biological data displaying means, and
comment data storing means, wherein
the age data acquiring means acquires age data of a user,
the biological data acquiring means acquires at least two kinds of biological data other than the age data from the user, the biological data displaying means displays the acquired biological data of the user in a graph region whose axes represent these two kinds of biological data, the comment data storing means stores comment data related to at least either of these two kinds of biological data in relation to age, and the biological data displaying means displays the comment data corresponding to the age data of the user. Thus, since the biological data of the user are displayed in the graph region whose axes represent the biological data and the comment corresponding to the age data of the user is displayed for at least either of these two kinds of biological data, an appropriate guideline for health care based on the age of the user can be presented to the user.

Further, each of the two kinds of biological data may be any of a body weight, a body mass index, a body fat mass, a body fat percentage, a total body water, a body water percentage, a muscle mass, a muscle percentage, a bone mass, a bone density, a basal metabolic rate and BCM. Thus, since the reference data or comment data corresponding to the age data of the user are displayed for these biological data, an appropriate guideline for health care based on the age of the user can be presented to the user.

EMBODIMENTS

Figure 2:
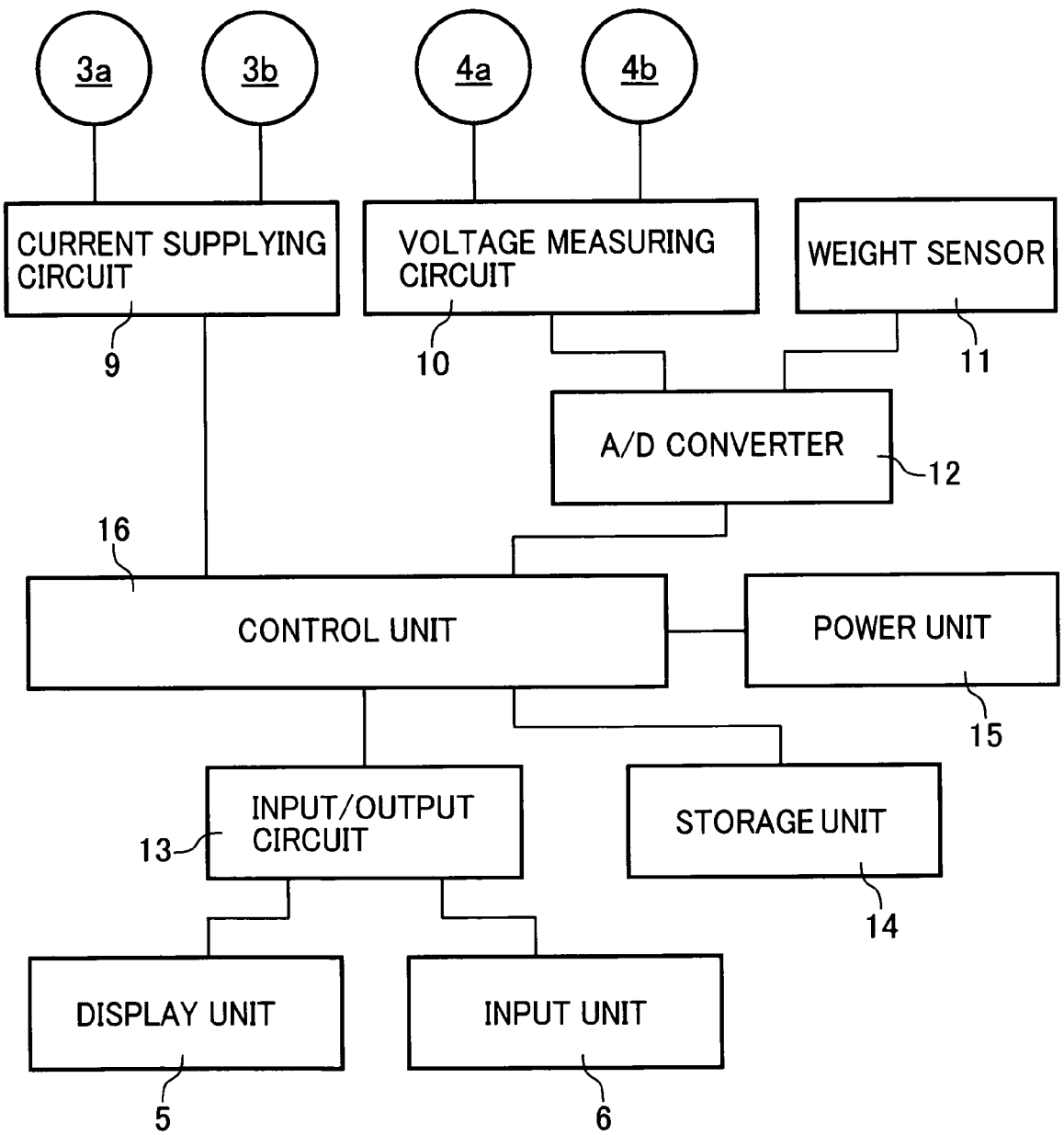
FIG. 2 is a block diagram illustrating the constitution of electric circuits in the biological data acquiring apparatus of FIG. 1.
Figure 3:
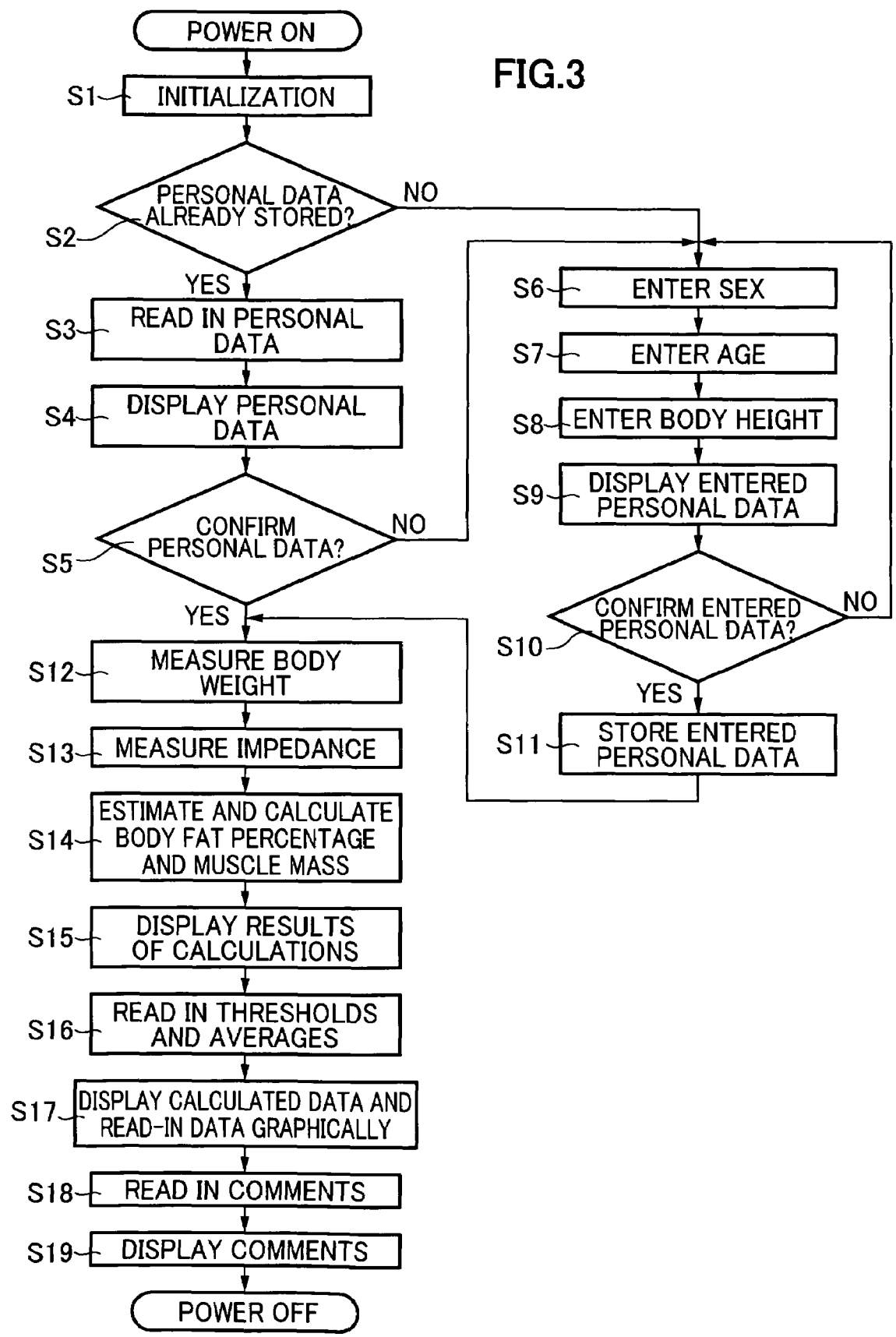
FIG. 3 is a flowchart illustrating a flow of control processes performed by the biological data acquiring apparatus of FIG. 1.
Figure 4:
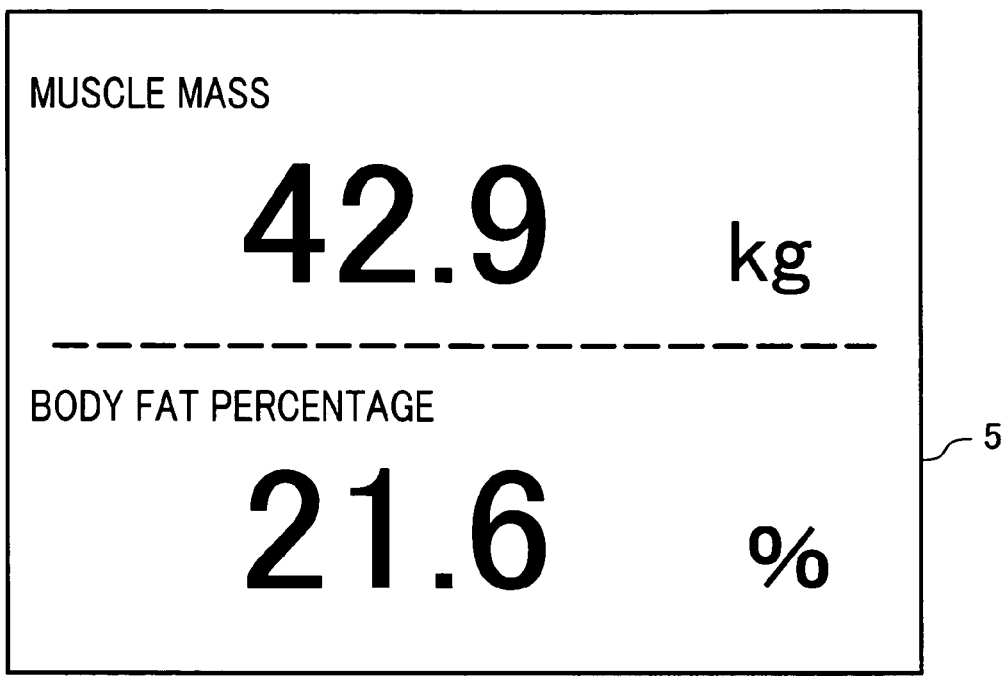
FIG. 4 is a diagram showing an example of screen displays in the biological data acquiring apparatus of FIG. 1.
Figure 5:
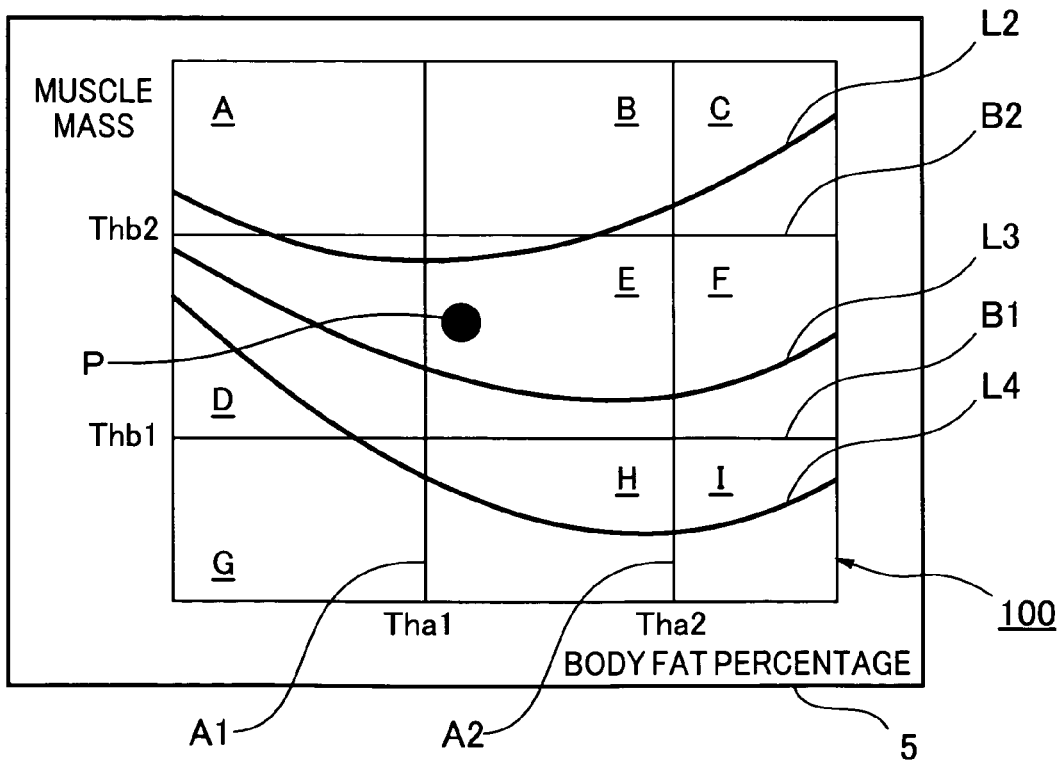
FIG. 5 is a diagram showing another example of screen displays in the biological data acquiring apparatus of FIG. 1.

Hereinafter, a suitable embodiment of the present invention will be described by use of the drawings. FIG. 1 is an external perspective view of a biological data acquiring apparatus 1 according to the present invention. FIG. 2 is a block diagram showing a brief description of the constitution of electric circuits incorporated in the biological data acquiring apparatus 1. FIG. 3 is a flowchart illustrating a flow of control processes performed by the biological data acquiring apparatus 1. FIGS. 4 to 6 are diagrams showing examples of screen displays in the biological data acquiring apparatus 1.

As shown in FIG. 1, the biological data acquiring apparatus 1 is an improved version of a so-called scale with a body fat monitor which has already been commercially available as a variety of products which measure the body weight and bioelectrical impedance of a user and calculate biological data such as a body fat percentage, a body water percentage, a visceral fat mass, a muscle mass, a bone density, a basal metabolic rate and BCM. Its main body 2 comprises a base 2a and a platform 2b which is placed on the base 2a. On the top surface of the platform 2b, current supplying electrodes 3a and 3b for passing an alternating current between the bottoms of both feet of a user, measurement electrodes 4a and 4b for measuring a voltage (potential difference) occurring between the bottoms of both feet with the alternating current passed therebetween, a display unit 5 which comprises a known liquid crystal screen and is used for displaying biological data acquired by the biological data acquiring apparatus 1, and an input unit 6 which is used by a user to enter sex, age, a body height and the like (hereinafter generically referred to as "personal data" in the present embodiment) are provided.

The input unit 6 comprises selection keys 6a and 6b which are used for selecting input data and a determination key 6c which is used for determining input data. Further, on a side of the main body 2, personal keys 7 which comprise four keys 7a, 7b, 7c and 7d for retrieving already entered personal data if any and a power key 8 are provided.

Further, as shown in FIG. 2, inside the main body 2 of the biological data acquiring apparatus 1, a current supplying circuit 9 which is connected to the above current supplying electrodes 3a and 3b, a voltage measuring circuit 10 which is connected to the above measurement electrodes 4a and 4b, a weight sensor 11 which generates a voltage corresponding to the body weight of a user when the user stands on the top surface of the platform 2b, an A/D converter 12 which converts voltages from the voltage measuring circuit 10 and the weight sensor 11 into digital signals, an input/output circuit 13 which is connected to the above display unit 5 and the above input unit 6, a storage unit 14 for storing entered personal data and acquired biological data, a power unit 15 which incorporates a battery, and a control unit 16 which is electrically connected to these current supplying circuit 9, A/D converter 12, input/output circuit 13, storage unit 14 and power unit 15 are provided.

In such a constitution, the control unit 16 incorporates a known arithmetic unit (CPU) and executes a control program stored in the above storage unit 14 in advance so as to perform various control processes such as control of accepting input of personal data from the above input unit 6, control of measuring the body weight of a user by use of the above weight sensor 11, control of measuring the bioelectrical impedance of the user by use of the above current supplying electrodes 3a and 3b and the above measurement electrodes 4a and 4b, control of estimating, calculating and acquiring the body fat percentage and muscle mass of the user as two kinds of biological data from these personal data, body weight and bioelectrical impedance, and control of displaying these body fat percentage and muscle mass on the above display unit 5. Although the biological data acquiring apparatus 1 in the present embodiment acquires a body fat percentage and a muscle mass as two kinds of biological data, these biological data may be any of a body weight, a body mass index, a body fat mass, a body fat percentage, a total body water, a body water percentage, a muscle mass, a muscle percentage, a bone mass, a bone density, a basal metabolic rate and BCM.

As shown in FIG. 3, when a user presses down the power key 8 so as to turn on the biological data acquiring apparatus 1, the control unit 16, firstly, initializes the whole biological data acquiring apparatus 1 in STEP S1. By this initialization process, data which were temporarily stored in the storage unit 14 upon execution of the previous control processes, a timer count value and the like are initialized.

Then, when the user presses down any of the personal keys 7a, 7b, 7c and 7d, the control unit 16 determines in STEP S2 whether personal data corresponding to the pressed personal key is stored in the storage unit 14. When the personal data is stored, the control unit 16 reads in the personal data in STEP S3 and then displays the personal data on the display unit 5 together with options (for example, "Yes" and "No") to be selected by the user for confirmation of the personal data in STEP S4. Then, when the user selects an option which affirms the displayed personal data by operating the selection keys 6a and 6b and determination key 6c of the input unit 6 in STEP S5, the control unit 16 proceeds to STEP S12. Meanwhile, when it is determined in STEP S2 that the personal data is not stored in the storage unit 14 or when the user selects an option which disaffirms the displayed personal data in STEP S5, the control unit 16 proceeds to STEP S6.

In STEP S6, the control unit 16 displays a message urging the user to enter the sex of the user on the display unit 5, and when the user enters sex by operating the input unit 6, the control unit 16 proceeds to STEP S7. In STEP S7, the control unit 16 displays a message urging the user to enter the age of the user on the display unit 5, and when the user enters age by operating the input unit 6, the control unit 16 proceeds to STEP S8. It is also acceptable that the user enters a certain range of age, e.g., "twenties", "thirties", "middle age", "old age" or the like, as the age. In STEP S8, the control unit 16 displays a message urging the user to enter the body height of the user on the display unit 5, and when the user enters the body height by operating the input unit 6, the control unit 16 proceeds to STEP S9. In STEP S9, the control unit 16 displays the user's sex, age and body height which have been entered by the control processes of STEPS S6 to S8 on the display unit 5 together with options to be selected by the user for confirmation of the personal data, just as in STEP S4. Then, in STEP S10, when the user selects an option which affirms the displayed sex, age and body height by operating the input unit 6, the control unit 16 proceeds to STEP S11 so as to store the displayed sex, age and body height in the storage unit 14 as personal data corresponding to the personal key pressed down by the user and then proceeds to STEP S12. Meanwhile, when the user selects an option which disaffirms the displayed sex, age and body height in STEP S10, the control unit 16 returns to STEP S6.

In STEP S12, the control unit 16 displays on the display unit 5 a message urging the user to stand on the top surface of the platform 2b with the toe side of the left foot bottom in contact with the above current supplying electrode 3a, the heel side of the left foot bottom in contact with the above voltage measuring electrode 4a, the toe side of the right foot bottom in contact with the above current supplying electrode 3b and the heel side of the right foot bottom in contact with the above voltage measuring electrode 4b. Then, when the user stands on the top surface of the platform 2b by following the message, the control unit 16 measures the body weight of the user based on a voltage detected by the weight sensor 11.

Then, in STEP S13, the control unit 16 supplies an alternating current to between both feet of the user from the current supplying circuit 9 via the current supplying electrodes 3a and 3b, detects a voltage (potential difference) between both feet of the user by the measurement electrodes 4a and 4b via the voltage measuring circuit 10, and determines the bioelectrical impedance of the user from the values of the supplied current and detected voltage based on the Ohm's law.

Then, in STEP S14, the control unit 16 performs calculations of the body fat percentage and muscle mass of the user in accordance with given regression formulae by use of, as variables, the personal data retrieved in STEP S3 or entered in STEPS S6 to S8, the body weight measured in STEP S12 and the bioelectrical impedance measured in STEP S13. As such regression formulae, various regression formulae have already been developed for various biological data such as a total body water (body water percentage), a bone mass, a basal metabolic rate and BCM, in addition to those for estimating and calculating a body fat percentage (body fat mass) and a muscle mass (muscle percentage), and regression formulae according to biological data to be acquired can be used as appropriate. As for a body mass index, it can be calculated as body weight/(body height)$^2$.

Then, in STEP S15, the control unit 16 displays the body fat percentage and muscle mass estimated and calculated in STEP S14 on the display unit 5 as shown in FIG. 4. In FIG. 4, the muscle mass is displayed on the upper side of the display unit 5, and the body fat percentage is displayed on the lower side thereof. The user associated with displays in FIG. 4 and FIG. 5 to be described later is a male with a body height of 154 cm, a body weight of 58 kg and an age of 67.

Then, in STEP S16, the control unit 16 retrieves thresholds and referential lines acquired by using smoothing methods which are used for a graphical representation to be described later, from the storage unit 14.

The thresholds in the present embodiment are a threshold Tha1 and a threshold Tha2 for a body fat percentage and a threshold Thb1 and a threshold Thb2 for a muscle mass, and it is predetermined that values not larger than the threshold Tha1 imply "thin", values not smaller than the threshold Tha2 imply "obese", values not larger than the threshold Thb1 imply "muscle reduction", and values not smaller than the threshold Thb2 imply "athlete". These thresholds are stored in the storage unit 14 for each age range, i.e., a youngster range (7 to 17 years old), a young man range (18 to 35 years old), a middle age range (36 to 59 years old) and an old age range (60 years old or older) The control unit 16 reads in thresholds Tha1, Tha2, Thb1 and Thb2 of an age range to which the user belongs, based on the user's age retrieved in STEP S2 or entered in STEP S7.

The number and meanings of the above thresholds can be set to any number and any meanings other than those described above. The above age ranges may be broader or narrower age ranges, or the thresholds may be provided for each age. Alternatively, it is also acceptable that in place of (or in addition to) such thresholds, the average of body fat percentages and the average of muscle masses for each age or each age range are acquired from a considerable number of subjects ranging from youngsters to elderly people and stored in the storage unit 14 in advance and the control unit 16 reads in these values.

Meanwhile, the above referential lines acquired by using smoothing methods are curves (youngster range: L1, young man range: L2, middle age range: L3, and old age range: L4) obtained by plotting body fat percentages and muscle masses acquired in advance from a considerable number of subjects ranging from youngsters to elderly people in a graph region to be described later for each of the same age ranges as those for the above thresholds and smoothing the plotted data for each age range. Further, the referential lines acquired by using smoothing methods are stored in the storage unit 14 for each age range, and the control unit 16 reads in a referential line acquired by using smoothing methods L4 that corresponds to an age range to which the user belongs, based on the user's age retrieved in STEP S2 or entered in STEP S7.

In the present embodiment, the control unit 16 reads in not only the referential line acquired by using smoothing methods of the age range to which the user belongs but also referential lines acquired by using smoothing methods of age ranges whose body fat percentages and muscle masses are very close to those of the user so as to make the graphical representation to be described later easier to understood. Further, it is needless to say that the referential lines acquired by using smoothing methods can be provided for each age, as in the case of the above thresholds and averages.

Then, in STEP S17, the control unit 16 displays the body fat percentage and muscle mass of the user which have been estimated and calculated in STEP S14 and the thresholds and referential line acquired by using smoothing methods corresponding to the age of the user which have been read in in STEP S16 on the display unit 5 graphically as shown in FIG. 5. That is, in a graph region 100 whose horizontal axis represents a body fat percentage and vertical axis represents a muscle mass, the body fat percentage and muscle mass of the user are displayed as an intersection point P. Further, the thresholds Tha1, Tha2, Thb1 and Thb2 corresponding to the age of the user are displayed as section lines A1 (Tha1), A2 (Tha2), B1 (Thb1) and B2 (Thb2) which divide the graph region into nine sections A to I. Further, the referential line acquired by using smoothing methods of the age range to which the user belongs is displayed as L4. In addition, as referential lines acquired by using smoothing methods to which the body fat percentage and muscle mass (intersection point P) of the user are very close, the referential line acquired by using smoothing methods L2 of the youngster range and the referential line L3 acquired by using smoothing methods of the middle age range are displayed.

Then, in STEP S18, the control unit 16 retrieves comment data to be used for comment display to be described later from the storage unit 14. The comment data is stored in the storage unit 14 in advance for each of the sections A to I divided by the above section lines A1, A2, B1 and B2 and each of the same age ranges as those for the above thresholds and referential lines acquired by using smoothing methods. The control unit 16 reads in comment data corresponding to the section to which the body fat percentage and muscle mass of the user belong and the age range to which the user belongs.

Then, in STEP S19, the control unit 16 displays the comment data read in STEP S18 as shown in FIG. 6. FIG. 6A shows a display example for the aforementioned 65-year-old user. Meanwhile, FIG. 6B shows a display example for a 25-year-old user having the same body fat percentage and muscle mass as those of the above elderly user. Thus, even if the values of estimated and calculated body fat percentages and muscle masses are the same, comments corresponding to the age (age range) of a user are displayed.

After displaying the above data in STEP S15, STEP S17 and STEP S19 for given times, the control unit 16 is automatically shut off, thereby completing all control processes.

Although one embodiment of the present invention has so far been described by use of the drawings, modes for carrying out the present invention are not limited thereto, and as described above as appropriate along with the embodiment, various modifications are possible. Further, for example, the above biological data acquiring apparatus 1 may also be constituted such that the above display unit 5 and input unit 6 are provided independently of the above main body 2 and connected to the main body 2 by electric cables or wireless communication such as infrared light. Further, the number of the above personal keys 7 may be more or less than 4, and each of the personal keys 7a, 7b, 7c and 7d may also function as a power key. Further, in addition to use of the input unit 6, a body height may be entered by attaching a body height meter comprising an electronic measure or the like to the main body 2 and measuring the body height by the body height meter. Alternatively, it is also possible that the weight sensor 11 is omitted from the main body 2 and the body weight of a user is entered from the input unit 6.

Further, in addition to the electrodes provided on the top surface of the main body 2 so as to measure a bioelectrical impedance between both feet of a subject, the above biological data acquiring apparatus 1 may adopt electrodes held by a subject with both hands so as to measure a bioelectrical impedance between both hands or electrodes for a foot and a hand which measure a bioelectrical impedance between a hand and a foot. Further, by adopting a so-called 8 electrode system comprising electrodes for both feet and electrodes for both hands, the biological data acquiring apparatus 1 can estimate and calculate a body fat percentage and a muscle mass in each body part such as the right arm, the right leg, the left arm or the left leg. Alternatively, it is also possible that the case itself corresponding to the main body 2 is rendered small and portable and electrodes to make contact with the palms or finger tips of a subject may be provided on the case so as to measure the bioelectrical impedance of the subject. Further, it is also possible that the electrodes are made applicable to the surface of a body so as to measure a bioelectrical impedance between any body parts (for example, between a shoulder and an elbow or between the back of a knee and a malleolus).

Further, the above biological data acquiring apparatus 1 may determine not only the body fat percentage and muscle mass of a user but also any two kinds of data out of various biological data such as a body fat mass, a muscle percentage, a total body water, a body water percentage, a bone mass, a basal metabolic rate and BCM by use of a measured bioelectrical impedance. Alternatively, it is also possible that the biological data acquiring apparatus 1 determines any one kind of data out of the above various biological data and the other kind of data is measured by known means such as MRI (magnetic resonance imaging device), x-ray CT (computerized transverse axial tomograph) or DEXA (dual energy x-ray absorption measuring device) and entered from the input unit 6. Alternatively, it is also possible that the weight sensor 11, the current supplying electrodes 3a and 3b and the measurement electrodes 4a and 4b are all omitted and both of the two kinds of biological data are measured by known means and entered from the input unit 6.

A biological data acquiring apparatus according to one aspect of the present invention comprises:
age data acquiring means,
biological data acquiring means,
biological data displaying means, and
reference data storing means, wherein
the age data acquiring means acquires age data of a user,
the biological data acquiring means acquires at least two kinds of biological data other than the age data from the user,
the biological data displaying means displays the acquired biological data of the user in a graph region whose axes represent these two kinds of biological data,
the reference data storing means stores reference data related to at least either of these two kinds of biological data in relation to age, and
the biological data displaying means displays the reference data corresponding to the age data of the user in the graph region. Thus, since the biological data of the user are displayed, together with the reference data corresponding to the age data of the user, in the graph region whose axes represent the two kinds of biological data, an appropriate guideline for health care based on the age of the user can be presented to the user.

The reference data are preferably thresholds predetermined for at least either of the two kinds of biological data, averages for each age or each age range which have been acquired from a number of subjects for at least either of the two kinds of biological data, or referential lines acquired by using smoothing methods which are obtained by plotting the two kinds of biological data acquired from a number of subjects in advance in the graph region for each age or each age range and then smoothing the plotted data. In these cases, since the biological data of the user are displayed in the graph region together with the thresholds, averages or referential lines corresponding to the age data of the user, an appropriate guideline for health care based on the age of the user can be presented to the user.

Alternatively, a biological data acquiring apparatus according to another aspect of the present invention comprises:
age data acquiring means,
biological data acquiring means,
biological data displaying means, and
comment data storing means, wherein
the age data acquiring means acquires age data of a user,
the biological data acquiring means acquires at least two kinds of biological data other than the age data from the user,
the biological data displaying means displays the acquired biological data of the user in a graph region whose axes represent these two kinds of biological data,
the comment data storing means stores comment data related to at least either of these two kinds of biological data in relation to age, and
the biological data displaying means displays the comment data corresponding to the age data of the user. Thus, since the biological data of the user are displayed in the graph region whose axes represent the biological data and the comment corresponding to the age data of the user is displayed for at least either of these two kinds of biological data, an appropriate guideline for health care based on the age of the user can be presented to the user.

Further, each of the two kinds of biological data may be any of a body weight, a body mass index, a body fat mass, a body fat percentage, a total body water, a body water percentage, a muscle mass, a muscle percentage, a bone mass, a bone density, a basal metabolic rate and BCM. Thus, since the reference data or comment data corresponding to the age data of the user are displayed for these biological data, an appropriate guideline for health care based on the age of the user can be presented to the user.

What is claimed is:
1. A biological data acquiring apparatus comprising:
age data acquiring means, biological data acquiring means,
biological data displaying means for displaying biological data, and
reference data storing means,
wherein the age data acquiring means acquires age data of a user,
wherein the biological data acquiring means acquires at least two kinds of biological data other than the age data from the user,
wherein the biological data displaying means displays the acquired biological data of the user in a graph region whose axes represent these two kinds of biological data,
wherein the reference data storing means stores reference data related to at least one of these two kinds of biological data in relation to age, and
wherein the biological data displaying means displays the reference data dividing the graph region into a plurality of sections corresponding to the age of the user.

2. The apparatus of claim 1, wherein the reference data are thresholds predetermined for at least either of the two kinds of biological data.

3. The apparatus of claim 1, wherein the reference data are averages for each age or each age range which have been acquired from a number of subjects for at least either of the two kinds of biological data.

4. A biological data acquiring apparatus comprising:
age data acquiring means,
biological data acquiring means,
biological data displaying means for displaying biological data, and
storing means,
wherein the age data acquiring means acquires age data of a user,
wherein the biological data acquiring means acquires at least two kinds of biological data other than the age data from the user,
wherein the biological data displaying means displays the acquired biological data of the user in a graph region whose axes represent these two kinds of biological data,
wherein the storing means stores reference data and comment data which are related to at least one of these two kinds of biological data in relation to age, and
wherein the biological data displaying means displays the reference data dividing the graph region into a plurality of sections corresponding to the age of the user and displays the comment data corresponding to each of the sections.

* * * * *

UNITED STATES PATENT AND TRADEMARK OFFICE
CERTIFICATE OF CORRECTION

| | | |
|---|---|---|
| PATENT NO. | : 7,252,635 B2 | Page 1 of 1 |
| APPLICATION NO. | : 10/863230 | |
| DATED | : August 7, 2007 | |
| INVENTOR(S) | : Shuji Itagaki | |

It is certified that error appears in the above-identified patent and that said Letters Patent is hereby corrected as shown below:

On the title page,

Item (56) References Cited, OTHER PUBLICATIONS", change "XP-002298438" to -- XP-002298436 --

Signed and Sealed this

Twenty-third Day of October, 2007

JON W. DUDAS
*Director of the United States Patent and Trademark Office*